United States Patent [19]
Curtet et al.

[11] Patent Number: 4,895,726
[45] Date of Patent: Jan. 23, 1990

[54] NOVEL DOSAGE FORM OF FENOFIBRATE

[75] Inventors: Bernard Curtet, Marsanny la Cote; Eric Teillaud, Talant; Philippe Reginault, Fontaine les Dijon, all of France

[73] Assignee: Fournier Innovation et Synergie, Paris, France

[21] Appl. No.: 299,073

[22] Filed: Jan. 19, 1989

[30] Foreign Application Priority Data

Feb. 26, 1988 [FR] France .................. 88 02359

[51] Int. Cl.⁴ .............................. A61K 9/64
[52] U.S. Cl. ..................... 424/456; 424/452; 424/458
[58] Field of Search ........... 424/456, 452, 458

[56] References Cited

U.S. PATENT DOCUMENTS 4,436,743  3/1984  Schönafinger et al. ............ 514/364
4,558,058 12/1985  Schöenfinger et al. ............ 514/342
4,629,624 12/1986  Grouiller et al. .................. 424/78

FOREIGN PATENT DOCUMENTS

82/01649  5/1982  European Pat. Off. .
0179583   4/1986  European Pat. Off. .
0239541   9/1987  European Pat. Off. .

*Primary Examiner*—Ellis P. Robinson
*Assistant Examiner*—Leon R. Horne
*Attorney, Agent, or Firm*—Fleit, Jacobson, Cohn, Price, Holman & Stern

[57] ABSTRACT

The present invention relates to a novel dosage form of fenofibrate containing fenofibrate and a solid surfactant which have been co-micronized.

It also relates to the method for the preparation of this dosage form and its use for improving the bioavailabity in vivo.

12 Claims, 1 Drawing Sheet

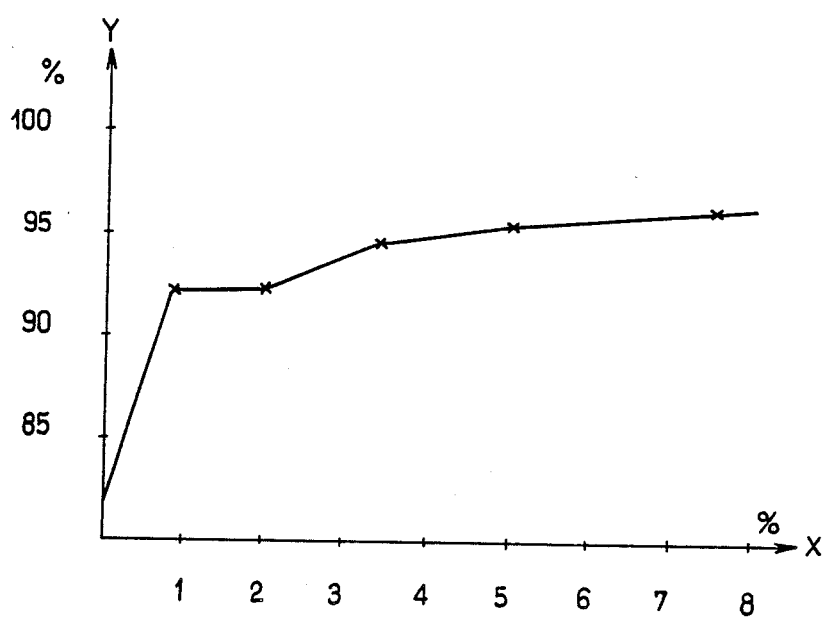

NOVEL DOSAGE FORM OF FENOFIBRATE

The present invention relates to a novel dosage form of fenofibrate. It relates more precisely to a therapeutic composition containing fenofibrate and ensuring an improved bioavailability, and to a method for the preparation of this composition.

Fenofibrate (international common name), which is recommended in the treatment of hyperlipidemia and hypercholesterolemia, corresponds to the nomenclature isopropyl 2-(4-(4-chlorobenzoyl)phenoxy)-2-methyl-propionate. The customary adult dosage is three gelatin capsules per day, each containing 100 mg of fenofibrate.

For the patient's comfort, it is advantageous to try and find a dosage form which has to be taken only once a day and whose psychological effect is identical to that obtained when multiple doses are taken. A gelatin capsule containing 300 mg of fenofibrate has therefore been proposed, the dosage recommended in this case being only one administration per day.

However, it is possible to try and improve the dosage form still further. It is known, in fact, that the bioavailability of fenofibrate is not equal to 100%. It is therefore desirable to develop a dosage form in which the bioavailability of the fenofibrate is improved and which can be administered only once a day.

It is known that the micronization of an active principle is capable of improving the dissolution of the said active principle in vivo, and hence its bioavailability. It is also known that the addition of a surfactant excipient to a formulation of an active principle is capable of improving the absorption and consequently the bioavailability of the said active principle.

It has now been discovered that the co-micronization of fenofibrate and a solid surfactant (i.e. the micronization of an intimate mixture of fenofibrate and a solid surfactant) makes it possible to improve the bioavailability of the fenofibrate to a significantly greater extent than that which would be achieved either by adding a surfactant, or by micronizing the fenofibrate on its own, or by intimately mixing the separately micronized fenofibrate and surfactant.

The present invention therefore proposes a novel therapeutic composition, presented in the form of gelatin capsules, which is useful especially in the oral treatment of hyperlipidemia and hypercholesterolemia, the said composition containing fenofibrate and a solid surfactant which have been co-micronized.

The recommended amount of fenofibrate is about 200 mg per therapeutic unit.

The surfactant will be selected from solid surfactants so that it can be co-micronized with the fenofibrate. An alkali metal sulfate of lauryl alcohol, for example sodium lauryl-sulfate (alternative name: sodium dodecyl-sulfate), will be preferred. The recommended amount of sodium lauryl-sulfate will be between 0.5% and 7% by weight, relative to the total weight of the formulation. The weight ratio surfactant/fenofibrate will advantageously be between about 0.75/100 and 10.5/100.

The co-micronization of the fenofibrate and the solid surfactant will advantageously be carried out in an accelerated air-jet mill until the powder obtained is such that the mean particle size is less than 15 μm, preferably less than 10 μm and particularly preferably less than 5 μm.

To obtain a powder which can be formulated into gelatin capsules, conventional filling, dispersing and flow-enhancing excipients, for example lactose, starch, polyvinylpyrrolidone and magnesium stearate, may be added to the co-micronizate of fenofibrate and solid surfactant.

According to the invention, a method for the preparation of a therapeutic composition containing fenofibrate and a solid surfactant is recommended which comprises:

(i) intimately mixing and then co-micronizing the fenofibrate and the solid surfactant, (ii) adding lactose and starch to the mixture obtained, (iii) converting the whole to granules in the presence of water, (iv) drying the granules until they contain no more than 1% of water, (v) grading the granules, (vi) adding polyvinylpyrrolidone and magnesium stearate to the graded granules, and (vii) filling gelatin capsules with the mixture obtained in stage (vi).

The invention will be understood more clearly from the description of the Preparative Examples which follow and from the description of the results obtained in comparative tests, which show that the invention is non-obvious.

PREPARATION I

For 100,000 gelatin capsules, each weighing 350 mg and containing 200 mg of fenofibrate, the amounts of products used are as follows:

| | |
|---|---|
| fenofibrate | 20.0 kg |
| sodium lauryl-sulfate | 0.7 kg |
| α-lactose monohydrate | 10.1 kg |
| pregelatinized starch | 3.0 kg |
| crosslinked polyvinyl-pyrrolidone | 0.7 kg |
| magnesium stearate | 0.5 kg |

The fenofibrate/sodium lauryl-sulfate mixture is co-micronized in an air-jet micronizer to give a powder with a median partizle size of 3 μm. The lactose and the starch are then added to this powder and the whole is converted to granules in the presence of 8.9% of distilled water, relative to the total weight of the mixture. The granules obtained in this way are dried for one day at 50° C. and then graded so as to retain only the particles with sizes less than or equal to 1000 μm. The polyvinylpyrrolidone and the magnesium stearate are then added and the whole is mixed until homogeneous. The powder obtained is used to fill size 1 gelatin capsules on an automatic machine with the compression set to a maximum of 150N.

PREPARATION II

The procedure indicated in Preparation I is followed using a fenofibrate/sodium lauryl-sulfate mixture with a median particle size of 6–7 μm.

PREPARATION III

For 100,000 size 1 gelatin capsules, each weighing 297 mg and containing 200 mg of active principle, the amounts of products are as follows:

| | |
|---|---|
| fenofibrate | 20.0 kg |
| sodium lauryl-sulfate | 0.3 kg |
| α-lactose monohydrate | 6.8 kg |
| pregelatinized starch | 1.5 kg |

-continued

| | |
|---|---|
| crosslinked polyvinyl-pyrrolidone | 0.6 kg |
| magnesium stearate | 0.5 kg |

The procedure is analogous to that used for Preparation I, the co-micronization of the fenofibrate/sodium lauryl-sulfate mixture being such that the median particle size is 6–7 μm and the granulation being carried out in the presence of 10% of distilled water, relative to the weight of the fenofibrate/sodium lauryl-sulfate/lactose/starch mixture.

PREPARATION IV

Following a procedure analogous to that described in Preparation I, using a co-micronized mixture of fenofibrate and sodium lauryl-sulfate with a median particle size of 6–7 μm, the formulations collated in Table I below were prepared:

TABLE I

COMPOSITION (in mg) PER GELATIN CAPSULE

| INGREDIENT | FORMULATION | | | | | |
|---|---|---|---|---|---|---|
| | A | B | C | D | E | F |
| Fenofibrate | 200 | 200 | 200 | 200 | 200 | 200 |
| Na lauryl-sulfate | 0 | 3 | 7 | 12 | 17.5 | 26.5 |
| Lactose | 108 | 105 | 101 | 95 | 90.5 | 83.5 |
| Starch | 30 | 30 | 30 | 30 | 30 | 30 |
| Polyvinylpyrrolidone | 7 | 7 | 7 | 7 | 7 | 7 |
| Mg stearate | 5 | 5 | 5 | 5 | 5 | 5 |
| Percentage of Na lauryl-sulfate | 0 | 0.86 | 2 | 3.4 | 5 | 7.53 |

Taking these formulations, the dissolution curve shown in FIG. 1 was plotted, the percentage of dissolved fenofibrate (Y) being given as a function of the percentage of sodium lauryl-sulfate contained in the formulation (X). The dissolution kinetics are determined, as specified in the European Pharmacopoeia, using a rotating-vane apparatus, the eluent consisting of water and 0.1M sodium lauryl-sulfate. The fenofibrate is determined by UV spectrophotometry at 282 nm. The curve in FIG. 1 is given by the values obtained after 20 minutes.

These results show that 82% of fenofibrate is dissolved at a sodium lauryl-sulfate concentration of 0%, 87% of fenofibrate is dissolved at a concentration of 0.5%, 92% of fenofibrate is dissolved at a concentration of 1% and a maximum dissolution of 95 to 96% of fenofibrate is obtained as from a sodium lauryl-sulfate concentration of 4%.

The dissolution curves were also plotted, in a continuous-flow cell with a flow rate of 20 ml/min of 0.1M sodium lauryl-sulfate, for formulations containing co-micronized fenofibrate and sodium lauryl-sulfate (NaLS), by comparison with micronized fenofibrate and with formulations obtained by intimately mixing separately micronized fenofibrate and lauryl-sulfate. The comparison is made by means of T 50%, i.e. the time required for 50% of the fenofibrate to dissolve. The results obtained are collated in Table II below:

TABLE II

| | VALUE OF THE T 50% TIMES (in minutes) | | |
|---|---|---|---|
| INGREDIENTS | A | B | C |
| Micronized pure fenofibrate | 37.165 | 37.165 | 0 |
| Fenofibrate + 1% of NaLS | 18.01 | 8.62 | −52.14 |
| Fenofibrate + 3% of NaLS | 23.75 | 12.68 | −46.61 |
| Fenofibrate + 5% of NaLS | 20.35 | 11.425 | −43.86 |
| Fenofibrate + 7% of NaLS | 14.5 | 10.76 | −25.79 |

Notes
A mixture of micronizates
B co-micronization of the mixture of ingredients
C variation $\frac{B - A}{A} \times 100$ (in %)

These results show that the T 50% of the fenofibrate is very significantly reduced (hence the dissolution rate of the fenofibrate is very significantly increased) when the fenofibrate and the sodium lauryl-sulfate are co-micronized, compared with the mixture of separately micronized fenofibrate and sodium lauryl-sulfate and compared with fenofibrate alone.

The dissolution rate of fenofibrate is correlated with the bioavailability of fenofibrate, which increases with the dissolution rate. The above results shown that it was not within the understanding of those skilled in the art to prepare a therapeutic composition characterized by the co-micronization of fenofibrate and a solid surfactant.

These results have been confirmed in clinical trials. Fenofibrate was administered to groups of healthy subjects, (a) in the form of a single administration (1 gelatin capsule) of 300 mg of non-micronized fenofibrate (marketed under the tradename "LIPANTHYL 300") and (b) in the form of a single administration of 200 mg of co-micronized fenofibrate obtained according to Preparation III described above. Blood samples are taken from the subjects at regular intervals and one of the active metabolites—2-[4-(4-chlorobenzoyl)phenoxy]-2-methylpropionic acid—is determined. The curve showing the concentration of this metabolite as a function of time is plotted and the area under the curve [AUC(0-∞)], expressed in mg/l.h, is calculated.

The results obtained are shown in Table III below:

TABLE III

| BIOAVAILABILITY PARAMETER | FENOFIBRATE 200 mg (1) | FENOFIBRATE 300 mg (2) |
|---|---|---|
| AUC(0-∞)(mg/l.h) | 174.15 ± 48.67 | 168.85 ± 57.68 |
| C max (m/l) | 10.86 ± 2.13 | 10.39 ± 2.89 |
| t max (h) | 5.97 ± 2.50 | 5.52 ± 1.70 |
| t ½ (h) | 15.13 ± 4.27 | 17.79 ± 8.77 |

Notes
(1) co-micronized fenofibrate (200 mg)
(2) non-micronized fenofibrate (300 mg)

The results in Table III show that there is not a statistically significant difference between the in vivo bioavailability of 200 mg of co-micronized fenofibrate according to the invention and 300 mg of non-micronized fenofibrate (which is currently the preferred dosage form for a single daily administration). In other words, co-micronized fenofibrate at a 200 mg dose is bioequivalent to non-micronized fenofibrate at a 300 mg dose.

According to another aspect of the invention, a method for improving the bioavailability of fenofibrate in vivo is recommended, the said method comprising co-micronization of the fenofibrate and a solid surfactant, the said co-micronization being carried out by micronization of a fenofibrate/solid surfactant mixture until the particle size of the powder obtained is less than 15 μm and preferably less than or equal to 5 μm.

What is claimed is:

1. A therapeutic composition, which is presented in the form of gelatin capsules and which is useful especially in the oral treatment of hyperlipidemia and hypercholesterolemia, said composition containing a co-micronized mixture of particles of fenofibrate and a solid surfactant, wherein the mean particle size of said co-micronized mixture is less than 15 μm.

2. The therapeutic composition according to claim 1 wherein the weight ratio surfactant/fenofibrate is between about 0.75/100 and 10.5/100.

3. The therapeutic composition according to claim 1 wherein the amount of fenofibrate is equal to 200 mg per therapeutic unit.

4. The therapeutic composition according to claim 1, wherein the solid surfactant is sodium lauryl-sulfate.

5. The therapeutic composition according to claim 4, wherein the amount of sodium lauryl-sulfate is between 0.5 and 7% by weight, relative to the total weight of the formulation.

6. The therapeutic composition according to claim 1, wherein said mean particle size is less than or equal to 10 μm and said solid surfactant is sodium lauryl-sulfate.

7. The therapeutic composition according to claim 1, which also contains excipients such as dispersants, fillers and flow enhancers.

8. A method for the manufacture of a therapeutic composition according to claim 1, which comprises:
   (i) intimately mixing and then co-micronizing the fenofibrate and a solid surfactant,
   (ii) adding lactose and starch to the mixture obtained,
   (iii) converting the whole to granules in the presence of water,
   (iv) drying the granules until they contain no more than 1% of water,
   (v) grading the granules,
   (vi) adding polyvinylpyrrolidone and magnesium stearate, and
   (vii) filling gelatin capsules.

9. The method according to claim 8, wherein the mean particle size of the co-micronized fenofibrate and sodium lauryl-sulfate is less than 15 μm.

10. A method for improving the bioavailability of fenofibrate in vivo, which comprises co-micronization of the fenofibrate and a solid surfactant, the said co-micronization being carried out by micronization of a fenofibrate/solid surfactant mixture until the particle size of the powder obtained is less than 15 μm.

11. A method for treatment of hyperlipidemia or hypercholesterolemia comprising orally administering the therapeutic composition of claim 6 to a patient.

12. The method of treatment of claim 11, wherein said particle size is less than or equal to 5 μm.

* * * * *

(12) REEXAMINATION CERTIFICATE (4423rd)
United States Patent
Curtet et al.

(10) Number: US 4,895,726 C1
(45) Certificate Issued: Aug. 28, 2001

(54) DOSAGE FORM OF FENOFIBRATE

(75) Inventors: Bernard Curtet, Marsanny la Cote; Eric Teillaud, Talant; Philippe Reginault, Fontaine les Dijon, all of (FR)

(73) Assignee: Fournier Industrie et Sante (FR)

Reexamination Request:
No. 90/005,586, Dec. 13, 1999

Reexamination Certificate for:
Patent No.: 4,895,726
Issued: Jan. 23, 1990
Appl. No.: 07/299,073
Filed: Jan. 19, 1989

(30) Foreign Application Priority Data

Feb. 26, 1988 (FR) .................................. 88 02359

(51) Int. Cl.$^7$ ............... A61K 9/64; A61K 9/48; A61K 9/54; A61K 31/235
(52) U.S. Cl. ............ 424/456; 424/452; 424/458; 514/543
(58) Field of Search ................. 424/456, 452, 424/458; 514/543

(56) References Cited

U.S. PATENT DOCUMENTS

| | | | |
|---|---|---|---|
| 4,344,934 | 8/1982 | Martin et al. | 424/80 |
| 4,412,986 | 11/1983 | Kawata et al. | 424/80 |
| 4,721,709 | 1/1988 | Seth et al. | 514/221 |
| 4,800,079 | 1/1989 | Boyer | 424/482 |
| 5,827,536 | 10/1998 | Laruelle | 424/451 |
| 5,880,148 | * 3/1999 | Edgar et al. | . |
| 6,074,670 | * 6/2000 | Stamm et al. | . |
| 6,180,138 | * 1/2001 | Engh et al. | . |

FOREIGN PATENT DOCUMENTS

| | | |
|---|---|---|
| 0179583A1 | 4/1986 | (EP) . |
| 0239541A2 | 9/1987 | (EP) . |
| 0256933A1 | 2/1988 | (EP) . |
| 0757911A1 | 2/1997 | (EP) . |
| 0793958-A2 | * 9/1997 | (EP) . |
| 2617047-A1 | * 12/1988 | (FR) . |
| WO82/01649 | 5/1982 | (WO) . |
| WO87/00428 | 1/1987 | (WO) . |

OTHER PUBLICATIONS

Ben–Amor et al., Augmentation of the Bioavailability of a Hypolipemic Agent for Incorporation Into a Liquid–Containing Gel, Congr. Int. Technol. Pharm., 5th (1989), vol. 3, 190–9.*

Improving the dissolution of active principles. Why? How? Boullay, STP PHARMA 1 (4) 287–340 (1985) and translation.

Physical Chemical Properties of Drugs, 1980, "Solubility and Partitioning in Drug Design", pp. 207–229.

(List continued on next page.)

*Primary Examiner*—Thurman K. Page

(57) ABSTRACT

The present invention relates to a novel dosage form of fenofibrate containing fenofibrate and a solid surfactant which have been co-micronized.

It also relates to the method for the preparation of this dosage form and its use for improving the bioavailabity in vivo.

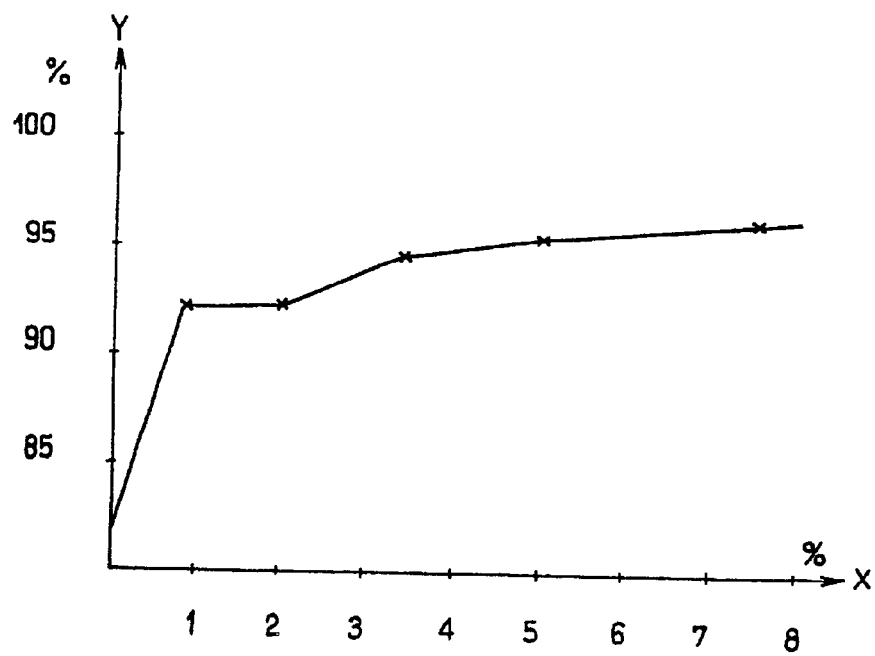

OTHER PUBLICATIONS

Galenic Pharmacy, 6$^{th}$ Edition, 1992, "III—Dissolution", Prof. Y. Cohen, pp. 127–131.

Galenica 2 Biopharmacie, 2$^{nd}$ Edition, 1982, Chapter 10, Sections 1–5, pp. 519–525.

Vidal 1995, 71e Edition, various pages containing Enantone; Gevatran; Praxilene; Seglor; and Zoladex.

Tools for Structure Activity Relationships User's Guide, 1993, Understanding Tsar.

Dictionnaire Vidal 63e Edition, 1987, p. 882 containing Lipanthyl® 300.

Giroud et al, Pharmacologie Clinique, "Factors Influencing Biostability", pp. 131–135.

Gelenica Pharmacy, vol. III, New Edition, Liege University, A. Denoel et al, "Solid divisional . . . ", 1968, p. 41.

Remington's Pharmaceutical Sciences, Fourteenth Edition, 1970, "Pharmaceutical Necessities", Chapter 71, pp. 1316–1348.

G. Boullay, STP Pharma 1 (4), "Microgrinding and dissolution" pp. 296–299, 1985.

Müzel et al, Galenisches Praktikum, Stuttgart 1959, "14.2.2 The Formation of a Coating with Insoluble . . . ", pp. 374, 412–415.

Riestchei, Angewandte Biopharmazie, Stuttgart 1973, "Dissolution rate . . . ", pp. 293–302.

Galencia 2 Biopharmacie, 2$^{nd}$ Edition, 1982, Chapter 4, pp. 151–159 and 335 regarding dissolution.

Letter from Lab Service S.A. dated Jul. 30, 1999 from George Boullay.

* cited by examiner

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

* * * * *